United States Patent
Wei et al.

(10) Patent No.: US 10,493,301 B2
(45) Date of Patent: Dec. 3, 2019

(54) THERMAL ABLATION SYSTEM

(71) Applicant: KONINKLIJKE PHILIPS N.V., Eindhoven (NL)

(72) Inventors: Juan Wei, Eindhoven (NL); Jianhua Zhang, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 15/316,888

(22) PCT Filed: Jun. 4, 2015

(86) PCT No.: PCT/EP2015/062488
§ 371 (c)(1),
(2) Date: Dec. 7, 2016

(87) PCT Pub. No.: WO2015/193119
PCT Pub. Date: Dec. 23, 2015

(65) Prior Publication Data
US 2017/0100608 A1  Apr. 13, 2017

(30) Foreign Application Priority Data

Jun. 20, 2014  (WO) ............... PCT/CN2014/080393
Nov. 5, 2014   (EP) ................................ 14191901

(51) Int. Cl.
*A61N 7/02* (2006.01)
*A61B 5/055* (2006.01)
(Continued)

(52) U.S. Cl.
CPC .............. *A61N 7/022* (2013.01); *A61B 5/055* (2013.01); *A61B 5/4836* (2013.01); *A61B 34/10* (2016.02);
(Continued)

(58) Field of Classification Search
CPC ........ A61B 2034/104; A61B 2090/374; A61B 34/10; A61B 5/055; A61B 5/4836; A61B 90/37; A61N 7/02; A61N 7/022
See application file for complete search history.

(56) References Cited

U.S. PATENT DOCUMENTS 6,241,725 B1 *  6/2001  Cosman ............. A61B 18/1477
                                                    600/41
6,575,969 B1 *  6/2003  Rittman, III ....... A61B 18/1482
                                                    128/898
(Continued)

FOREIGN PATENT DOCUMENTS

EP     2423700 A1   2/2012
EP     2500740 A1   9/2012
(Continued)

OTHER PUBLICATIONS

Luo E Tal "Blood Oxygen Level Dependent MRI in Observation of Oxygen Uptaking Chracteristics of Primary . . . " Chinese Journal of Medical Imaging Technology 2011, col. 17 No. 5.
(Continued)

*Primary Examiner* — Michael F Peffley
(74) *Attorney, Agent, or Firm* — Sherry Austin (57) ABSTRACT

A thermal ablation includes a thermal ablation apparatus configured to perform thermal ablation on a targeted tissue according to plan data of a treatment during a therapy mode of the thermal ablation system. An MR apparatus is configured to perform T2* weighted MR imaging of the targeted tissue to assess a therapeutic response of the thermal ablation during an assessment mode of the thermal ablation system. A control apparatus is configured to switch the thermal ablation system between the therapy mode and the assessment mode. The thermal ablation apparatus is activated to perform the thermal ablation in the therapy mode. The thermal ablation apparatus is deactivated to terminate
(Continued)

the thermal ablation and the MR apparatus is activated to perform the T2* weighted MR imaging in the assessment mode.

16 Claims, 4 Drawing Sheets

(51) Int. Cl.
*A61B 5/00* (2006.01)
*A61B 34/10* (2016.01)
*A61B 90/00* (2016.01)
*A61N 7/00* (2006.01)

(52) U.S. Cl.
CPC ............... *A61B 90/37* (2016.02); *A61N 7/02* (2013.01); *A61B 2034/104* (2016.02); *A61B 2090/374* (2016.02); *A61N 2007/0086* (2013.01)

(56) References Cited

U.S. PATENT DOCUMENTS

| | | | | |
|---|---|---|---|---|
| 7,553,309 | B2* | 6/2009 | Buysse | A61B 18/1206 606/34 |
| 7,871,406 | B2* | 1/2011 | Nields | A61B 18/18 606/27 |
| 8,131,339 | B2* | 3/2012 | Bonn | A61B 18/1206 600/410 |
| 8,369,930 | B2* | 2/2013 | Jenkins | A61B 5/055 600/410 |
| 9,622,813 | B2* | 4/2017 | Krugman | A61B 5/055 |
| 10,010,723 | B2* | 7/2018 | Koehler | A61N 5/025 |

FOREIGN PATENT DOCUMENTS

| | | |
|---|---|---|
| EP | 2636368 A1 | 9/2013 |
| WO | 0135825 A1 | 5/2001 |
| WO | 2012049628 A1 | 4/2012 |
| WO | WO2012147733 A1 | 11/2012 |
| WO | 2014066853 A1 | 5/2014 |
| WO | 2014170138 A1 | 10/2014 |

OTHER PUBLICATIONS

Burgess et al "High Intensity Focused Ultrasound for Dissolution of Clots in a Rabbit Model of Embolic Stroke" PLOS One 2012.

Chen et al "Prostate Cancer Detection:Comparison of T2-Weighted Imaging, . . . " Acta Radiologica, 2008, vol. 49, (5) p. 602-610.

Ying Z. et al, "The Oxygenation in Different Funaki Types of Uterine Fibroids and Their Change After MR-HIFU Treatment: Evaluation with T2", Proceedings of International Society for magnetic Resonance in Medicine, 21, p. 4312, 2013.

Hancock H. at al., "Cellular MRI Assessment of Magnetic Fluorescent Bead Labeled Macrophage Accumulation Following High Intensit Focused Ultrasound (HIFU) Induced Damage in a Murine Model", Proceedings on International Society for magnetic Resonance in Medicine, 5: 7, p. 4266, 2010.

\* cited by examiner

THERMAL ABLATION SYSTEM

CROSS REFERENCE TO RELATED APPLICATIONS

This application is a U.S. national phase application of International Application No. PCT/EP2015/062488, filed on Jun. 4, 2015, which claims the benefit of EP Application Serial No. 14191901.9 filed on Nov. 5, 2014 and PCT/CN2014/080393 filed Jun. 20, 2014 both of which are incorporated herein by reference.

FIELD OF THE INVENTION

The invention relates to a thermal ablation system, in particular to a thermal ablation system with therapeutic response assessment.

BACKGROUND OF THE INVENTION

Recently, there is increasing interest and development of non-invasive or minimally invasive methods to kill tumor cells. In particular, thermal ablation is being investigated as an alternative and/or supplement to traditional methods of tumor destruction. Several methods have been developed and are being developed for various forms of cancer including, among others, cancers of the breast, prostate, lung, kidney, and liver. Methods of introducing localized heat include Radio Frequency Ablation (RFA), microwave therapy, extracorporeal or direct focused ultrasound, laser ablation, and other interstitial heat delivery methods including therapeutic ultrasound applicators. In particular, the use of high intensity focused ultrasound (HIFU) is currently being used as an approach for thermal therapeutic intervention for uterine fibroids and has been examined for possible uses in the treatment of liver, brain, prostate, and other cancerous lesions. The use of ultrasound is desirable because it allows the non-invasive treatment of deep tissues with little or no effect on overlying organs. Ultrasound therapy for tissue ablation works by sonicating a tissue of interest with high intensity ultrasound that is absorbed and converted into heat, thereby raising the temperature of the targeted tissues. As the temperature rises above 55 degree centigrade, coagulative necrosis of the tissues occurs resulting in immediate cell death. The transducers used in therapy can be outside the body or be inserted into the body e.g. through blood vessels, urethra, rectum etc.

Nowadays, magnetic resonance guided high intensity focused ultrasound (MR-HIFU) therapeutic system is commercially available to make the therapy procedure safe and efficient. In particular, MR-HIFU ablation is a promising technology in the field of oncologic intervention, e.g., ablation of benign tumors in the uterus, so-called uterine fibroids.

Currently, contrast-enhanced MR imaging is considered the 'golden standard' for assessing therapeutic response of MR-HIFU ablation, expressed as non-perfused volume (NPV), immediately after MR-HIFU therapy. However, contrast-enhanced MR imaging requires injection of GD-contrast agent (GD-DOTA). Although inject of contrast agent is relatively well tolerated, it will inevitably bring discomfortable feelings. Even worse, for patients with history of allergic and nephrotic dysfunction, reactions after injection of contrast agent may be severe and life-threatening. Due to intravenous injection of contrast agent, contrast-enhanced MR imaging can only be performed to assess the treatment after the HIFU therapy is completed, which means the assessment result cannot be used to improve the HIFU therapy in a real-time manner. Although EP2636368A1 provided a medical apparatus capable of modifying the treatment plan of the heating system using the magnetic resonance data, the modification is based on thermographic MR images to ensure that adequate heating is accomplished at the target zone while safeguarding that other critical anatomic structures are left intact. There is no teaching how to modify treatment plan of the HIFU therapy according to therapeutic response of HIFU ablation to improve the therapy efficacy.

SUMMARY OF THE INVENTION

It is an object of the invention to improve patient comfort and/or patient safety during the assessment of thermal ablation treatment.

Embodiments of the invention provide a thermal ablation system, a method for operating the thermal ablation system, and a method for determining the thermal ablation volume in the independent claims. Embodiments of the invention are given in the dependent claims. Embodiments of the invention use T2* weighted MR imaging to assess the therapeutic response of thermal ablation and optionally modify the treatment plan to improve the therapy. Although, the conventional contrast-enhanced MR imaging can assess the treatment after the therapy is completed, injection of contrast agent is undesirable and thermal ablation is unchangeable. This invention solves these problems by performing T2* weighted MR imaging to assess the thermal ablation. Hereby patient comfort and/or safety can be improved.

Embodiments of the invention provide a thermal ablation system. The thermal ablation system comprises a thermal ablation apparatus configured to perform thermal ablation on a targeted tissue according to plan data of a treatment during a therapy mode of the thermal ablation system, a MR apparatus configured to perform a T2* weighted MR imaging for the targeted tissue to assess a therapeutic response of the thermal ablation during an assessment mode of the thermal ablation system, a control apparatus configured to switch the thermal ablation system between the therapy mode and the assessment mode. The thermal ablation apparatus is activated to perform the thermal ablation in the therapy mode, and the thermal ablation apparatus is deactivated to terminate the thermal ablation and the MR apparatus is activated to perform the T2* weighted MR imaging in the assessment mode. Advantageously, the T2* weighted MR imaging reliefs patients from injection of contrast agent. Without injection of contrast agent, assessment of the therapeutic response of thermal ablation can be performed flexibly at the follow-up procedure or during the treatment in a real-time manner. Assessment in the real-time manner further enables modification of the treatment plan to improve the therapy efficacy.

According to an embodiment of the present invention, the control apparatus is further configured to modify the plan data of the treatment plan based on an assessment result of the therapeutic response of the thermal ablation during the assessment mode. Advantageously, the therapy efficacy can be improved with modified plan data.

According to an embodiment of the present invention, the thermal ablation system is switched from the therapy mode to the assessment mode upon the completion of the treatment in accordance with the plan data.

According to an embodiment of the present invention, the thermal ablation system is switched from the therapy mode to the assessment mode during the treatment to assess the therapeutic response of the HIFU ablation in a real-time manner. Advantageously, the operator can choose to modify the plan data of the treatment plan based on an assessment result of the therapeutic response of the thermal ablation. Upon completion of plan data modification, the thermal ablation system is switched back to the therapy mode to perform the thermal ablation according to the modified plan data. Advantageously, the therapy efficacy is enhanced with the modified plan data.

According to an embodiment of the present invention, the MR apparatus is further configured to guide the thermal ablation during the therapy mode of the thermal ablation system. Advantageously, it is ensured that adequate heating is accomplished at the intended tissues while safeguarding that other critical anatomic structures are left intact.

According to an embodiment of the present invention, the thermal ablation system further comprises a graphical user interface for displaying a T2* weighted MR image to visualize non-perfusion volume of the thermal ablation. Advantageously, the non-perfusion volume can be easily and clearly visualized by the operator to make the treatment assessment and interact with the thermal ablation system.

In another aspect, the present invention provides a method for operating a thermal ablation system. The method comprises the steps of performing thermal ablation on a targeted tissue according to plan data of a treatment during a therapy mode of the thermal ablation system, performing a T2* weighted MR imaging for the targeted tissue to acquire a T2* weighted MR image during an assessment mode of the thermal ablation system, assessing a therapeutic response of the thermal ablation based upon the T2* weighted MR image during the assessment mode of the thermal ablation system, and switching the thermal ablation system between the therapy mode and the assessment mode. The thermal ablation is activated and the T2* weighted MR imaging is deactivated in the therapy mode, and the thermal ablation is deactivated and the T2* weighted MR imaging is activated in the assessment mode.

According to an embodiment of the present invention, the targeted tissue comprises uterine fibroids.

According to an embodiment of the present invention, the method further comprises modifying the plan data of the treatment plan based on an assessment result of the therapeutic response of the thermal ablation during the assessment mode.

According to an embodiment of the present invention, the thermal ablation system is switched from the therapy mode to the assessment mode upon completion of the treatment in accordance with the plan data.

According to an embodiment of the present invention, the thermal ablation system is switched from the therapy mode to the assessment mode during the treatment to assess the therapeutic response of the thermal ablation in a real-time manner and modify the plan data of the treatment plan based on an assessment result of the therapeutic response of the thermal ablation. The thermal ablation system is switched back to the therapy mode to perform the thermal ablation according to the modified plan data upon completion of plan data modification.

In another aspect, the present invention provides a method for determining a thermal ablation volume of tissue treated with thermal ablation treatment. The method comprises performing a T2* weighted MR imaging from a region comprising tissue treated with thermal ablation treatment to acquire a T2* weighted MR image, and determining the thermal ablation volume of the treated tissue by means of the T2* weighted MR image.

In another aspect, the present invention provides a computer program product. The computer program product comprises machine executable instructions to be executed by a microprocessor of a thermal ablation system. The execution of the machine executable instructions causes the microprocessor to control thermal ablation on a targeted tissue according to plan data of a treatment during a therapy mode of the thermal ablation system, acquire a T2* weighted MR image of the targeted tissue during an assessment mode of the thermal ablation system, assess a therapeutic response of the thermal ablation based upon the T2* weighted MR image during the assessment mode of the thermal ablation system; and switch the thermal ablation system between the therapy mode and the assessment mode, wherein the thermal ablation is activated and the T2* weighted MR imaging is deactivated in the therapy mode, and wherein the thermal ablation is deactivated and the T2* weighted MR imaging is activated in the assessment mode.

Advantageously, the T2* weighted MR imaging reliefs patients from injection of contrast agent. Without injection of contrast agent, assessment of the therapeutic response of thermal ablation can be performed flexibly at the follow-up procedure or during the treatment in a real-time manner. Assessment in the real-time manner further enables modification of the treatment plan to improve the therapy efficacy.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION OF THE EMBODIMENTS

Detailed description of the present invention is given below in connection with the accompanying drawings.

Figure 1:
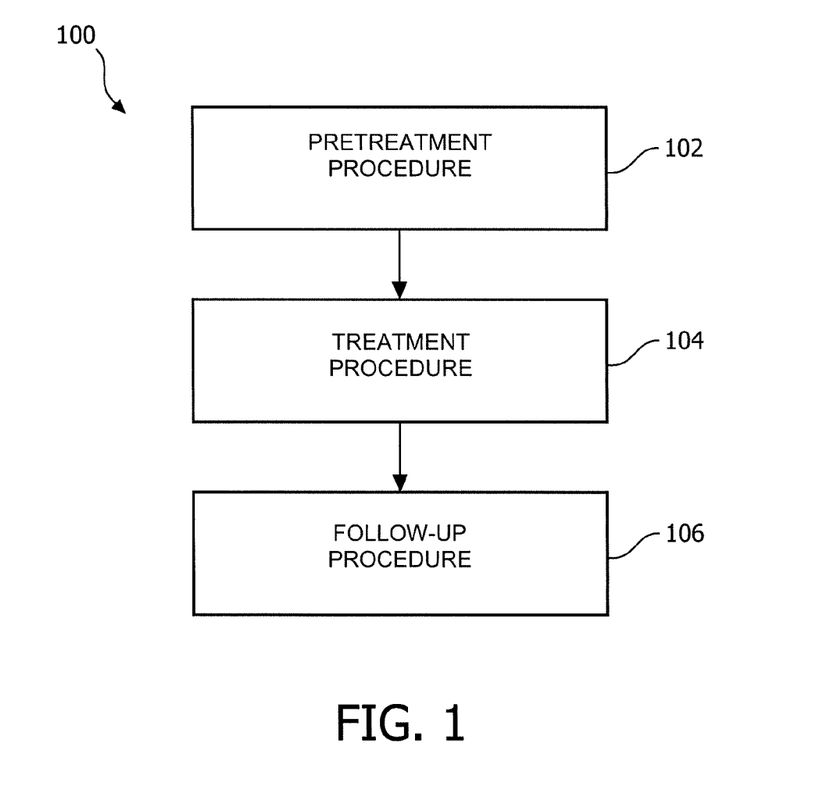
FIG. 1 illustrates a flow chart 100 for performing a thermal therapy according to one embodiment of the present invention.

FIG. 1 illustrates a flow chart 100 for performing a thermal therapy according to one embodiment of the present invention. For the purpose of simplifying the description but not limitation, the embodiment in FIG. 1 is described in the context of MR-HIFU therapy of uterine fibroids. The flow chart 100 includes a pretreatment procedure 102, a treatment procedure 104 and a follow-up procedure 106.

In the pretreatment procedure 102, a patient is evaluated with a clinical assessment, imaging and physical examination to decide whether the patent is a candidate from a technical feasibility aspect and also decide what treatment option (i.e., MR-HIFU, uterine fibroid embolization, myomectomy or hysterectomy) best meets the goals of the patient. Then, parameters of the fibroids within the uterus, such as size, location, number and T2 signal intensity, are evaluated to determine the feasibility of HIFU treatment. Although contrast-enhanced pretreatment MR examinations are not performed by all practices before MR-HIFU treatment, contrast enhancement can be helpful in the selection of fibroids targeted for treatment.

Upon completion of the pretreatment procedure 102, the treatment procedure 104 in accordance with plan data starts. In the example of MR-HIFU therapy, a focused ultrasound beam is directed towards the targeted fibroids. The ultrasound beam is used for heating a tumor through the skin and intervening tissue while MR imaging is used for monitoring the temperature distribution within the insonified region. Using the proton resonance frequency shift (PRFS) method, the temperature in tissues having a high water content can be monitored accurately. A linear shift of the proton resonance frequency is observed for the range of temperatures being used in HIFU system. In this range, MR thermometry is also reasonably sensitive. The reconstruction of thermographic MR images during ultrasound therapy is useful to provide feedback to ensure that adequate heating is accomplished at the intended location while safeguarding that other critical anatomic structures are left intact.

After the treatment procedure 104 completes the treatment in accordance with the plan data, T2* (T2 start) weighted MR imaging is performed to assess NPV, that is, to evaluate the occurrence of complications and the ablation results in the follow-up procedure 106. At MR imaging, when RF energy source is turned off, net magnetization vector realigns with the axis of static magnetic field B0 through the process of T1 recovery, during which the longitudinal magnetization recovers. At the same time, the transverse magnetization decays through additional mechanisms known as T2* decay and T2 decay. Different tissues have different T1, T2, and T2* values. Furthermore, T2* is dependent on the magnetic environment. Differences in T1, T2 and T2* in various tissues create differences in tissue contrast on images. Two key parameters-repetition time (TR) and echo time (TE)-affect contrast on MR images because they provide varying levels of sensitivity to differences in relaxation time between various tissues. T2* weighted MR imaging uses simple multi-slice fast field echo (MS FFE) sequence with medium TE to acquire the MR image.

Advantageously, without injection of contrast agent, T2* weighted MR imaging provides a simple and efficient solution for HIFU therapy assessment. As previously mentioned, the flow chart 100 for performing the HIFU therapy is described in connection with the embodiment of MR-HIFU therapy of uterine fibroids. In practices, the HIFU therapy as illustrated in FIG. 1 can be applied to various tissues or guided by different modalities or performed without image guidance through variation or modification to the pretreatment and treatment procedures 102 and 104. With these variation and modification, T2* weighted MR imaging can still be used in the follow-up procedure 106 to make treatment assessment.

Figure 2:
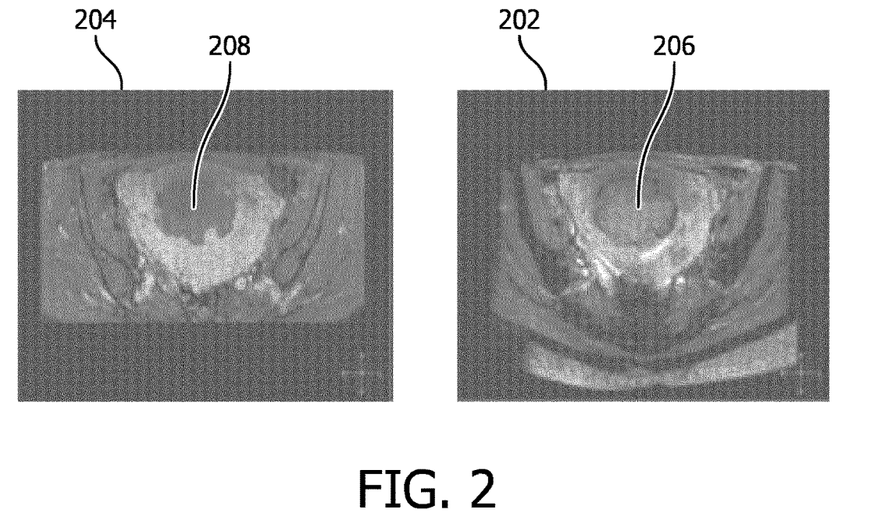
FIG. 2 illustrates a comparison of T2* weighted MR image and contrast-enhanced MR image at 1 month follow-up procedure according to one embodiment of the present invention.

FIG. 2 illustrates a T2* weighted MR image 202 acquired in the follow-up procedure 106 according to one embodiment of the present invention. Since contrast-enhanced MR imaging is considered the 'golden standard' for assessing therapeutic response of HIFU ablation, the T2* weighted MR image 202 is presented with comparison to a contrast-enhanced T1 weighted MR image 204 to demonstrate the effectiveness of T2* weighted MR imaging in treatment assessment.

In the embodiment of FIG. 2, at 1-month follow-up procedure, the T2* weighted MR image 202 is acquired before injection of contrast agent GD-DTPA and the contrast-enhanced T1 weighted MR image 204 is acquired three minutes after injection of contrast agent GD-DTPA. The geometric parameters of T2* weighted MR imaging and contrast-enhanced T1 weighted MR imaging protocols are the same, that is, the scanning location of both two protocols are the same with the same field of view (FOV), number of slices, slice thickness, gap and matrix. The detailed parameters of T2* weighted MR image 202 are as follows: turbo field echo (TFE)=17 axial slices; repetition time (TR)/echo time (TE)=837/24 ms; slice thickness=5 mm with 1 mm gap; field of view (FOV)=240×240 mm; matrix=320×250; flip angle=24°. The detailed parameters of contrast-enhanced T1 weighted MR image 204 are as follows: TFE=17 axial slices; TR/TE=500/10 ms; slice thickness=5 mm with 1 mm gap; FOV=240×240 mm; matrix=320×250; flip angle=90°.

The resulting images acquired through T2* weighted MR imaging and contrast-enhanced T1 weighted MR imaging are compared slice by slice at the same location in each patient. With reference to FIG. 2, the T2* weighted MR image 202 and the contrast-enhanced T1 weighted MR image 204 show a comparison result of a single slice as an example. On the image 202, a NPV region 206 inside uterine fibroids is visualized. On the image 204, a NPV region 208 inside uterine fibroids is visualized. Seen from FIG. 2, it can be observed that the boundary between NPV and normal tissue inside fibroids is more clearly shown on T2* weighed image 202 than contrast-enhanced T1 weighted MR image 204 due to a dark line margin. Actually, low signal intensity is detected around NPV of fibroids on T2* weighted images. Because of tissue necrosis in NPV due to HIFU ablation, the boundary between NPV and normal fibroids' tissue induces obvious inhomogeneity in magnetic field which could be susceptible to T2* weighted MR images. Therefore, NPV can be visualized with clear margin around due to the signal loss.

Furthermore, via lots of experiments and comparison, it is concluded that details around the margin shown on T2* weighted MR images are almost exactly the same with those on contrast-enhanced T1 weighted MR images. Results of quantitative measurement of NPV areas on both T2* weighted MR images and contrast-enhanced T1 weighted MR images show that they are very close to each other on every slice of fibroids' images in all patients. Meanwhile, paired-t-test analysis of NPV areas measurement between T2* weighted MR images and contrast-enhanced T1 weighted MR images show no significant differences between them (t=1.295, P=0.203>0.05). Therefore, by quantitative and statistical analysis, T2* weighted MR imaging without injection of contrast agent shows its feasibility of assessing ablated volumes inside fibroids as an alternative to the most commonly adopted 'golden standard' contrast-enhanced MR imaging.

Moreover, elimination of contrast agent injection enables T2* weighted MR imaging a practical tool in monitoring ablated volume of fibroids in a real-time manner during HIFU therapy in clinical applications. Thanks to real-time observation of ablated volume, treatment plan of HIFU therapy can be adjusted in accordance with assessment results and HIFU therapy can be performed repeatedly to improve the therapy efficacy.

Figure 3:
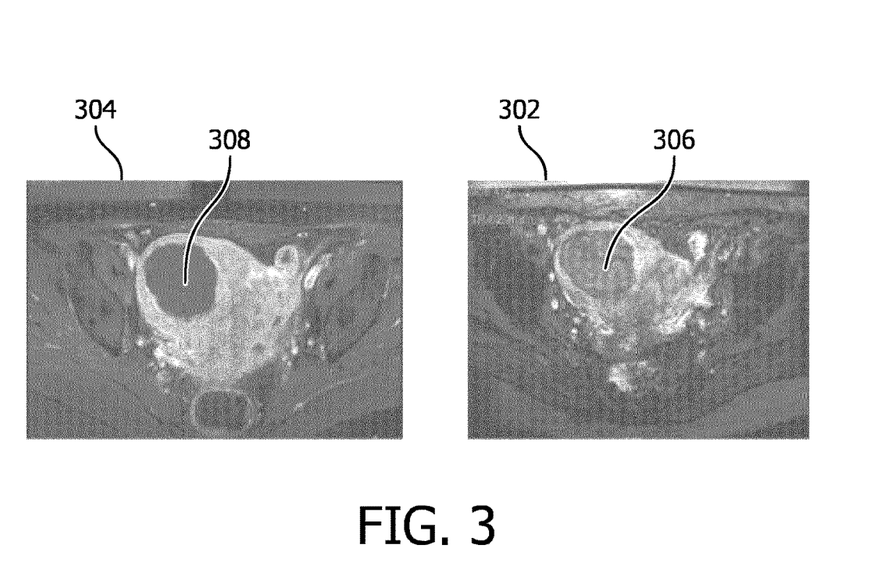
FIG. 3 illustrates a comparison of T2* weighted MR imaging and contrast-enhanced MR imaging immediately after HIFU therapy according to one embodiment of the present invention.

With reference to FIG. 3, a T2* weighted MR image 302 and a contrast-enhanced T1 weighted MR image 304 are acquired immediately after HIFU ablation when a condition and environment of targeted tissues is keeping the same as those during the HIFU ablation. On the image 302, a NPV region 306 inside uterine fibroids is visualized. On the image 304, a NPV region 308 inside uterine fibroids is visualized. Details around the margin shown on T2* weighted MR images are almost exactly the same with those on contrast-enhanced T1 weighted MR images. A comparison result between the T2* weighted MR image 302 and the contrast-enhanced T1 weighted MR image 304 further demonstrates the feasibility of T2* weighted MR images to assess ablated volumes inside fibroids. Since the targeted tissues are in a condition and environment similar to those during the therapy, it can be concluded that T2* weighted MR imaging can also be used during the treatment procedure.

Figure 4:
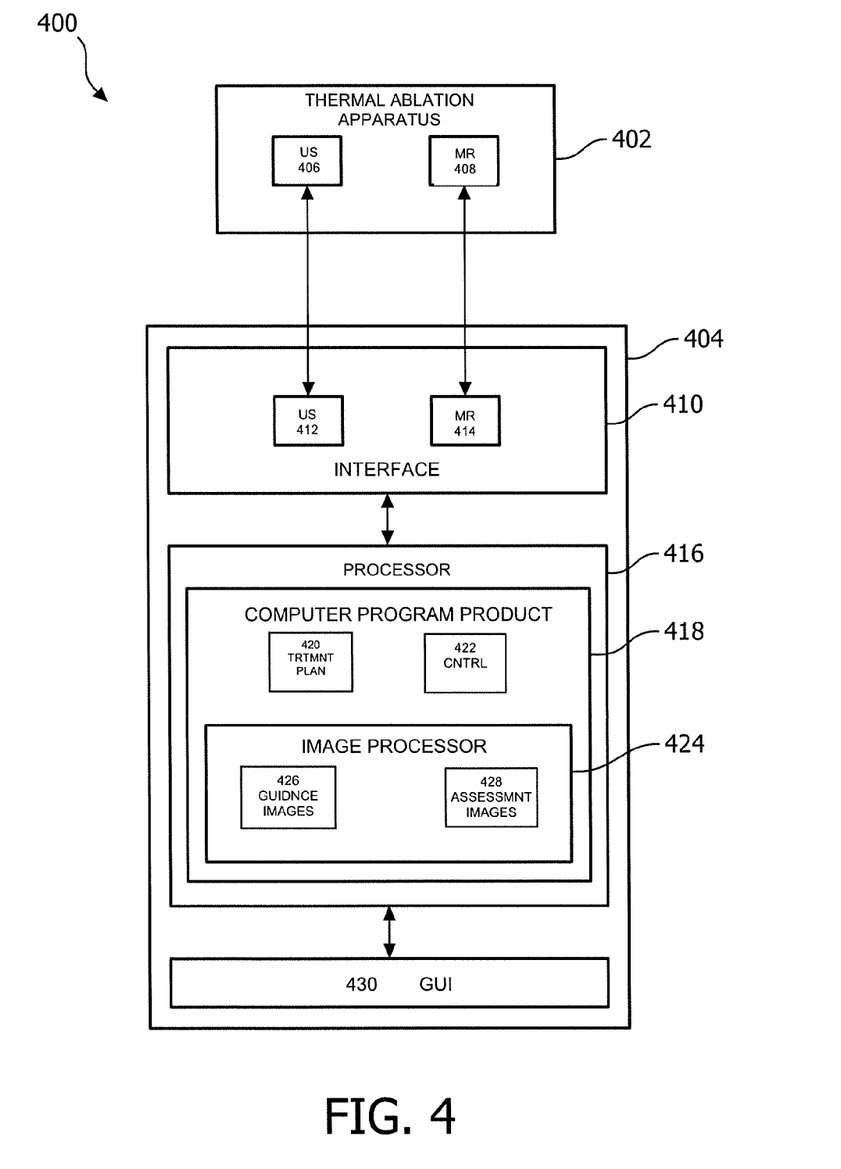
FIG. 4 illustrates a block diagram of a HIFU therapeutic system 400 according to one embodiment of the present invention.

FIG. 4 illustrates a block diagram of a thermal ablation system 400 according to one embodiment of the present invention. The HIFU therapeutic system 400 includes a thermal ablation apparatus 402 and a control apparatus 404. The thermal ablation apparatus 402 can be, but not limited to, RFA, microwave therapy, extracorporeal or direct focused ultrasound, and laser ablation. In the embodiment of FIG. 4, for the purpose of description but not limitation, the HIFU therapeutic apparatus 402 is an MR-HIFU therapeutic apparatus including a therapeutic ultrasound apparatus 406 and a magnetic resonance apparatus 408. The control apparatus 404 has a hardware interface 410 that is for interfacing to external hardware. The hardware interface 410 is able to send and receive data. The hardware interface 410 has a sub-component which is an ultrasound control interface 412 connected to the therapeutic ultrasound apparatus 406. The hardware interface 408 also has a magnetic resonance control interface 414 connected to the magnetic resonance apparatus 408. The hardware interface 410 is connected to a microprocessor 416. The microprocessor 416 is representative of any processing unit able to perform instructions in order to control the HIFU therapeutic apparatus 402. Examples would be a microprocessor, a controller, or an embedded system. There is a computer program product 418 comprising machine executable code which is able to be executed on the microprocessor 416.

The computer program product 418 comprises different executable instruction components or modules for performing different tasks. For example, the computer program product 418 comprises a treatment plan module 420 which encompasses a set of instructions or data for providing plan data to plan the HIFU therapy. The computer program product 418 further comprises a control module 422 to control the operation of the HIFU therapeutic apparatus 402 during the HIFU therapy in accordance with the plan data. More specifically with respect to the embodiment in FIG. 4, the control module 422 is able to control MR-HIFU therapy by controlling the therapeutic ultrasound apparatus 406 through the ultrasound control interface 412 and controlling the magnetic resonance apparatus 408 through the magnetic resonance control interface 414. The computer program product 418 also comprises an image processing module 424. The image processing module 424 is able to take raw magnetic resonance imaging data and turn these into magnetic resonance guiding images 426 for guiding the HIFU therapy and T2* weighted MR images 428 for assessing the HIFU therapy.

During the therapy operations, the control module 422 is able to switch the HIFU therapeutic apparatus 402 between a therapy mode and an assessment mode. In the therapy mode, the therapeutic ultrasound apparatus is activated to perform HIFU ablation in accordance with plan data output from the treatment plan module 420. More specifically, the magnetic resonance apparatus 408 acquires raw magnetic resonance imaging data to generate magnetic resonance guiding images 426. In accordance with the plan data, the therapeutic ultrasound apparatus 406 performs HIFU ablation concurrently under the guidance of the magnetic resonance guiding images 426. In the assessment mode, the therapeutic ultrasound apparatus 406 is deactivated to terminate HIFU ablation temporally. During the termination of HIFU ablation, the magnetic resonance apparatus 408 is activated to perform the T2* weighted MR imaging, e.g., using simple MS FFE sequence with medium TE, to acquire T2* weighted MR images 428. The treatment plan module 420 contains computer executable code which enables the microprocessor 426 to recognize the dark line margins of ablated volume automatically and therefore to assess the therapeutic response of HIFU ablation and modify the plan data in accordance with the assessment results. Upon completion of plan data modification, the HIFU therapeutic apparatus 402 is returned back to the therapy mode by activating the therapeutic ultrasound apparatus 406. Advantageously, the plan data of HIFU treatment can be modified repeatedly until a desirable assessment result is achieved to guarantee a successful HIFU ablation.

In one embodiment, the control apparatus 404 also comprises a graphical user interface 430. The graphical user interface 430 is able to interact with the computer program product 418 which runs on the microprocessor 416. The graphical user interface 430 is adapted for displaying the medical imaging images such as the magnetic resonance guiding images 426 and the T2* weighted MR images 428 in a format which an operator is able to understand. The graphical user interface 430 is also adapted for receiving selections from an operator. In the embodiment of FIG. 4 where the computer program product 418 is able to automatically recognize the ablated volume based upon the T2* weighted MR images 428 to assess the treatment result and modify the plan data accordingly, the graphical user interface 430 can also comprise a means for displaying a suggested plan data and possibly a means for an operator to edit it or to approve or disapprove of the treatment plan. Alternatively, the operator can select the ablated volume indicated by the T2* weighted MR images 428 manually through the graphical user interface 430, and the computer program product 418 assesses the treatment result and modifies the plan data based upon the ablated volume manually selected by the operator.

It would be understood by the skilled in the art that the HIFU therapeutic apparatus 402 is not necessarily guided by the magnetic resonance apparatus 408. Alternatively, the HIFU therapeutic apparatus can also be guided by an ultrasound apparatus or even without an image guidance apparatus. For ultrasound guided HIFU therapy, the image processing module comprises a component which is able to take ultrasound data and construct an ultrasound image. No matter whether the image guidance is adopted in connection with HIFU therapy or what kinds of imaging modality is used for image guidance, the T2* weighted MR imaging can still be performed during the temporal termination of HIFU ablation to assess the treatment result and modify the plan data. Upon the completion of plan data modification, the therapeutic ultrasound apparatus 406 is re-activated to continue the HIFU therapy in accordance with the modified therapy plan.

Figure 5:
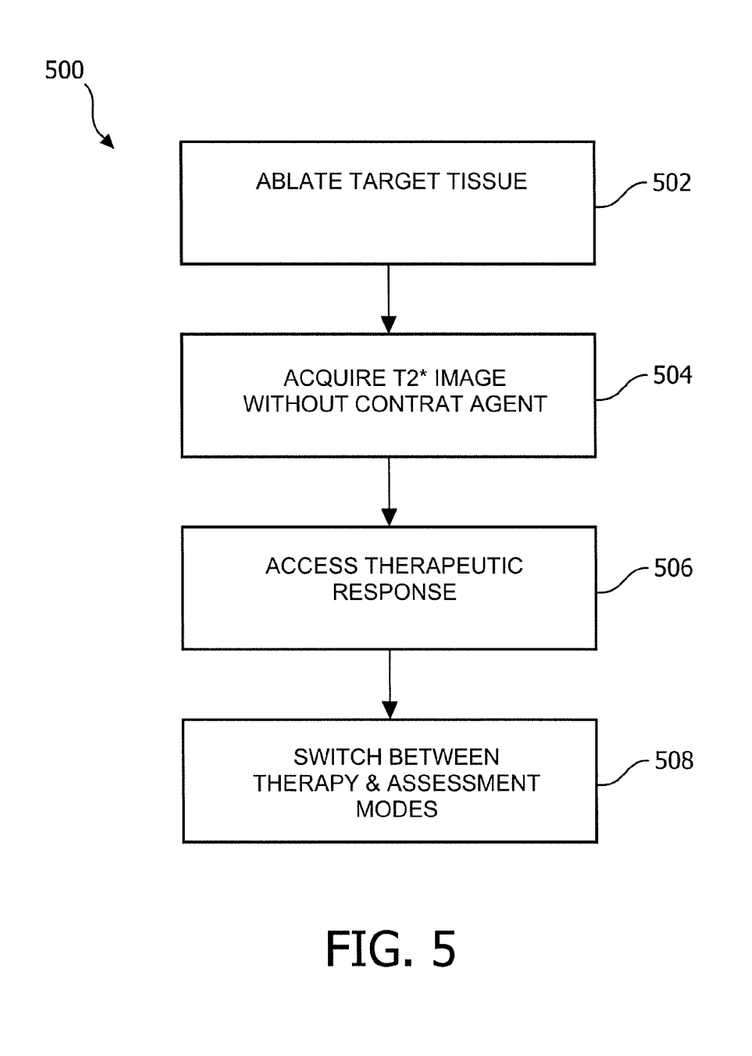
FIG. 5 illustrates a flow chart 500 for operating a thermal ablation system according to more embodiment of the present invention.

FIG. 5 illustrates a flow chart 500 for operating a thermal ablation system according to one embodiment of the present invention. FIG. 5 is described in combination with FIG. 1 and FIG. 4. At step 502, HIFU ablation is performed on a targeted tissue according to plan data of a treatment during a therapy mode of the HIFU therapeutic system. At step 504, T2* weighted MR imaging is performed for the targeted tissue to acquire a T2* weighted MR image during an assessment mode of the HIFU therapeutic system. At step 506, the therapeutic response of the HIFU ablation is assessed based upon the T2* weighted MR image during the assessment mode of the HIFU therapeutic system. At step 508, the HIFU therapeutic system is switched between the therapy mode and the assessment mode.

In the example of FIG. 4, during the therapy mode of the HIFU therapeutic system 400, the therapeutic ultrasound apparatus 406 is activated to perform HIFU ablation on a targeted tissue according to plan data output from the treatment plan module 420. With reference to FIG. 1, the targeted tissue is selected through the pretreatment procedure 102. Referring back to FIG. 4, the MR apparatus 408 is activated to perform the T2* weighted MR imaging to generate the T2* weighted MR images 428 during an assessment mode of the HIFU therapeutic system 400. In one embodiment, the treatment plan module 420 automatically recognize the ablated volume based upon the T2* weighted MR images 428 to assess the treatment result. In an alternative embodiment, the operator can select the ablated volume indicated by the T2* weighted MR images 428 manually through the graphical user interface 430, and the computer program product 418 assesses the treatment result based upon the ablated volume manually selected by the operator. The control module 422 is able to switch the HIFU therapeutic apparatus 402 between the therapy mode to perform the HIFU ablation and the assessment mode to perform the T2* weighted MR imaging. In one embodiment, the T2* weighted MR imaging is performed in the follow-up procedure 106 after the treatment procedure 104. In other words, the therapeutic response of HIFU ablation is assessed after the HIFU therapy is completed. In an alternative embodiment, the T2* weighted MR imaging is performed in the treatment procedure 104. In other words, the therapeutic response of HIFU ablation is assessed in a real-time manner. Thanks to real-time assessment, the treatment plan module 420 can modify the plan data based upon the assessment result to optimize the therapy efficacy.

It should be noted that the above-mentioned embodiments illustrated rather than limit the invention and that those skilled in the art would be able to design alternative embodiments without departing from the scope of the appended claims. The embodiments are illustrative rather than restrictive. It is intended that the invention include all modifications and variations to the illustrated and described embodiments within the scope and spirit of the invention. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the device claims enumerating several units, several of these units can be embodied by one and the same item of hardware or software. The usage of the words first, second and third, et cetera, does not indicate any ordering. These words are to be interpreted as names.

The invention claimed is:

1. A thermal ablation system comprising:
   a thermal ablation apparatus configured to perform thermal ablation on a targeted tissue in a patient according to plan data of a treatment during a therapy mode;
   a magnetic resonance (MR) apparatus configured to acquire a T2* weighted MR image without injection of a contrast agent of the targeted tissue to visualize an ablated volume due to the thermal ablation on the T2* weighted MR image during an assessment mode of the thermal ablation system; and
   a control apparatus or computer processor coupled to the thermal ablation apparatus and the MR apparatus and configured to switch the thermal ablation system between the therapy mode and the assessment mode, wherein the thermal ablation apparatus is activated to perform the thermal ablation in the therapy mode, and wherein the thermal ablation apparatus is deactivated to terminate the thermal ablation and the MR apparatus is activated to acquire the T2* weighted MR image without contrast agent injection in the assessment mode.

2. The thermal ablation system of claim 1, wherein the thermal ablation apparatus includes a high intensity focused ultrasound transducer disposed exterior to the patient and is configured to ablate the targeted tissue by transmitting high intensity ultrasound radiation focused on the targeted tissue through the skin of the patient.

3. The thermal ablation system of claim 1, wherein the control apparatus or computer processor is further configured to modify the plan data of the treatment plan based on the assessed ablated volume of the thermal ablation during the assessment mode.

4. The thermal ablation system of claim 1, wherein the control apparatus or computer processor is further configured to switch the thermal ablation system from the therapy mode to the assessment mode subsequent to completion of the treatment in accordance with the plan data.

5. The thermal ablation system of claim 1, wherein the control apparatus or computer processor is further configured to switch the thermal ablation system between the therapy mode and the assessment mode during the treatment to assess the ablated volume of the thermal ablation in a real-time manner and modify the plan data of the treatment plan based on the assessed ablated volume.

6. The thermal ablation system of claim 1, wherein the MR apparatus is further configured to guide the thermal ablation during the therapy mode of the thermal ablation system.

7. The thermal ablation system of claim 1, wherein a dark line margin of the ablated volume is visible on the T2* weighted MR image acquired without contrast agent injection.

8. The thermal ablation system of claim 1, further comprising:
   a graphical user interface configured to display the T2* weighted MR image acquired without contrast agent injection to visualize the ablated volume of the thermal ablation.

9. The thermal ablation system of claim 1, wherein the T2* weighted MR image acquired without contrast agent injection includes a dark line margin around the ablated volume and wherein the control apparatus or computer processor is further configured to recognize the dark line margin in the assessment mode.

10. A method for controlling a thermal ablation system which is configured to operate in a therapy mode and an assessment mode, wherein thermal ablation is activated to be performed on a target tissue according to plan data of a treatment during the therapy mode and is deactivated during the assessment mode, the method comprising:

performing without injection of a contrast agent of a T2* weighted magnetic resonance (MR) imaging of the targeted tissue to acquire a T2* weighted MR image without contrast agent during the assessment mode of the thermal ablation system;

visualizing an ablated volume of the thermal ablation on the T2* weighted MR image without contrast agent during the assessment mode of the thermal ablation system;

recognizing a dark line margin of the ablated volume in the T2* weighted MR image without contrast agent injection;

modifying the plan data of the treatment based on an assessment of the dark line margin of the ablated volume of the thermal ablation; and after modifying the plan data of the treatment, performing further ablation of the target tissue based on the modified plan data of the treatment.

11. The method of claim 10, wherein the targeted tissue is uterine fibroids.

12. The method of claim 10, further comprising:
modifying the plan data of the treatment plan based on the assessed ablated volume of the thermal ablation during the assessment mode.

13. The method of claim 10, further comprising switching the thermal ablation system from the therapy mode to the assessment mode upon completion of the treatment in accordance with the plan data.

14. The method of claim 10, further comprising:
switching the thermal ablation system from the therapy mode to the assessment mode during the treatment to assess the ablated volume of the thermal ablation in a real-time manner.

15. A method for thermal ablation of tissue with a thermal ablation system, comprising:

thermally ablating tissue with the thermal ablation system in accordance with treatment plan data from a treatment plan memory;

performing without injection of a contrast agent a T2* weighted magnetic resonance (MR) imaging of a region comprising tissue treated with a thermal ablation system, a boundary between necrotic tissue and non-necrotic tissue in the region inducing an inhomogeneity of a magnetic field applied during the MR imaging;

reconstructing a contrast agent free T2* weighted MR image of the region, the magnetic field inhomogeneity resulting in a dark line margin between the necrotic and non-necrotic tissue;

based on an assessment of the dark line margin, modifying the treatment plan data; and performing further thermal ablation in accordance with the modified treatment plan data.

16. A computer program product comprising machine executable instructions stored on a non-transitory computer readable medium to be executed by a microprocessor of a thermal ablation system, wherein the execution of the machine executable instructions causes the microprocessor to control thermal ablation on a targeted tissue according to plan data of a treatment during a therapy mode of the thermal ablation system;

acquire a T2* weighted MR image without injection of a contrast agent of the targeted tissue during an assessment mode of the thermal ablation system;

visualize an ablated volume of the thermal ablation on the T2* weighted MR image during the assessment mode of the thermal ablation system; and switch the thermal ablation system between the therapy mode and the assessment mode, wherein the thermal ablation is activated and the T2* weighted MR imaging without contrast agent injection is deactivated in the therapy mode, and wherein the thermal ablation is deactivated and the T2* weighted MR imaging without contrast agent injection is activated in the assessment mode.

* * * * *